(12) United States Patent
He et al.

(10) Patent No.: US 9,326,814 B2
(45) Date of Patent: May 3, 2016

(54) SYSTEM AND METHOD FOR PREDICTING LESION SIZE SHORTLY AFTER ONSET OF RF ENERGY DELIVERY

(75) Inventors: Ding Sheng He, Tyngsboro, MA (US); Michael Bosnos, Tucson, AZ (US); José M. Guillén-Rodríguez, Tucson, AZ (US); Frank I. Marcus, Tucson, AZ (US)

(73) Assignees: The Arizona Board of Regents on Behalf of the University of Arizona, Tucson, AZ (US); Boston Scientific Scimed Inc., Maple Grove, MN (US)

( * ) Notice: Subject to any disclaimer, the term of this patent is extended or adjusted under 35 U.S.C. 154(b) by 1371 days.

(21) Appl. No.: 12/882,780

(22) Filed: Sep. 15, 2010

(65) Prior Publication Data

US 2011/0066147 A1    Mar. 17, 2011

Related U.S. Application Data

(60) Provisional application No. 61/242,642, filed on Sep. 15, 2009.

(51) Int. Cl.
*A61B 18/10* (2006.01)
*A61B 18/14* (2006.01)
(Continued)

(52) U.S. Cl.
CPC ... *A61B 18/1492* (2013.01); *A61B 2017/00084* (2013.01); *A61B 2018/00357* (2013.01); *A61B 2018/00577* (2013.01); *A61B 2018/00702* (2013.01); *A61B 2018/00869* (2013.01); *A61B 2018/00875* (2013.01); *A61B 2034/104* (2016.02)

(58) Field of Classification Search
CPC .......... A61B 2018/00577; A61B 2018/00636; A61B 2018/00642; A61B 2018/00648; A61B 2018/00779; A61B 2018/00791; A61B 2018/00827; A61B 2018/00869; A61B 2018/00875; A61B 2018/00886; A61B 2018/00892; A61B 18/1206
See application file for complete search history.

(56) References Cited

U.S. PATENT DOCUMENTS

| 5,971,980 | A | 10/1999 | Sherman |
| 6,053,912 | A | 4/2000 | Panescu et al. |
| 6,423,057 | B1 * | 7/2002 | He et al. .................. 606/34 |

(Continued)

FOREIGN PATENT DOCUMENTS

WO    2009065140 A1    5/2009

OTHER PUBLICATIONS

Blouin LT, Marcus FI, Lampe L. Assessment of effects of radiofrequency energy fields and thermister location in an electrode catheter on the accuracy of temperature measurement. Pacing and Clinical Electrophysiology 1991;14:807-813.

(Continued)

*Primary Examiner* — Ronald Hupczey, Jr.
(74) *Attorney, Agent, or Firm* — Faegre Baker Daniels LLP

(57) ABSTRACT

Lesion size or volume prediction shortly after the onset of an ablation procedure can inform or control the ablation procedure. The prediction and/or control is made without regard to an actual detected temperature in the vicinity of the ablation electrodes. As a consequence, the system has utility with irrigated catheter constructions and other situations in which local irrigation in the vicinity of an ablation site would otherwise interfere with a prediction or control scheme that solely relies upon temperature measurements.

20 Claims, 5 Drawing Sheets

(51) Int. Cl.
  *A61B 17/00* (2006.01)
  *A61B 18/00* (2006.01)

(56) References Cited

U.S. PATENT DOCUMENTS

| | | | |
|---|---|---|---|
| 6,882,460 B2 | 4/2005 | Tsu et al. | |
| 7,001,383 B2 * | 2/2006 | Keidar | 606/41 |
| 7,306,593 B2 | 12/2007 | Keidar et al. | |
| 8,403,925 B2 * | 3/2013 | Miller et al. | 606/34 |
| 8,419,725 B2 * | 4/2013 | Haemmerich et al. | 606/32 |
| 2003/0060818 A1 | 3/2003 | Kannenberg et al. | |
| 2006/0034730 A1 | 2/2006 | Beyette, Jr. et al. | |
| 2007/0100666 A1 | 5/2007 | Stivoric et al. | |
| 2009/0149848 A1 | 6/2009 | Werneth et al. | |
| 2010/0152727 A1 | 6/2010 | Gibson et al. | |

OTHER PUBLICATIONS

Bosnos Michael, B.S.E.E., Guillen-Rodriguez, Jose M., M.S., He, Ding, S., M.D., Ph.D., and Marcus, Frank, M.D. Early Assessment of Biophysical Parameters Predicts Lesion Formation During RF Energy Delivery In Vitro. PACE 2010; 1-7.

Calkins H, Yong P, Miller JM, Olshansky B, Carlson M, Saul JP, Shoei K, et al. Catheter ablation of accessory pathways, atrioventricular nodal reentrant tachycardia, and the atrioventricular junction. Circulation 1999;99:262-270.

Dinerman JL, Berger RD, Calkins H. Temperature monitoring during radiofrequency ablation. J of Cardiovasc Electrophysiol 1996;7:163-173.

Eick OJ, Gerritse B, Schumacher B. Popping phenomena in temperature-controlled radiofrequency ablation: when and why do they occur? Pacing and Clinical Electrophysiol 2000; 23:253-258.

Everett TH, Lee KW, Wilson EE, Guerra JM, Varosy PD, Olgin JE. Safety profiles and lesion size of different radiofrequency ablation technologies: A comparison of large tip, open and closed irrigation catheters. J Cardiovasc Electrophysiol. 2009;20:325-335.

Fishbein MC, Meerbaum S, Rit J, Londo U, Kanmatsuse K, Mercier JC, Corday E, et al. Early phase acute myocardial infarct size quantification: validation of the triphenyl tetrazolium chloride tissue enzyme staining technique. Am Heart J; 1981;101:593-600.

He D, Bosnos M, Mays M, Marcus F. Assessment of Myocardial Lesion Size During in vitro Radiofrequency Catheter Ablation. IEEE Transactions in Biomedical Engineering 2003;50(6): 768-776.

Josephson ME, Schibgilla VH. Non-pharmacological treatment of supraventricular arrhythmias. Eur Heart J 1996;17:26-34.

Lillie RD, HJ Conn's Biological Stains, 9th edition. Baltimore, MD: Williams & Wilkins, 1977, pp. 225.

Nakagawa H, Yamanashi WS, Pitha JV, Arruda M, Wang X, Ohtomo K, Beckman KJ, et al. Comparison of in vivo tissue temperature profile and lesion geometry for radiofrequency ablation with a saline-irrigated electrode versus temperature control in a canine thigh muscle preparation. Circulation. 1995;91:2264-2273.

Nath S, Barber MJ. Update on the biophysics and thermodynamics of radiofrequency ablation. Cardiac Electrophysiology Review 1997;4:407-411.

Nath S, Haines DE, Biophysics and pathology of catheter energy delivery systems. Progress in Cardiovascular Diseases. 1995;37:185-204.

Petersen HH, Chen X, Pietersen A, Svendsen JH, Haunso S. Lesion dimensions during temperature-controlled radiofrequency catheter ablation of left site, electrode size, and convective cooling. Circulation 1999;99:319-325.

Schluter M, Kuck KH. Temperature-controlled radiofrequency current ablation—what temperature? European Heart Journal 1996;17:327-329.

Stagegaard N, Petersen HH, Cehn X, Svendsen JH. Indication of the radiofrequency induced lesion size by pre-ablation measurements. Europace 2005;7:525-534.

Stevensen WG, Wilber DJ, Natale A, Jackman WM, Marchlinski FE, Talbert T, Gonzales MD, et al. Irrigated radiofrequency catheter ablation guided by electroanatomic mapping for infarction: The multicenter thermocool ventricular tachycardia ablation trial. Circulation. 2008;118:2773-2782.

Willems S, Chen X, Kottkamp H, Hindricks G, Haverkamp W, Rotman B, Shenasa M, et al. Temperature-controlled radiofrequency catheter ablation of manifest accessory pathways. European Heart Journal 1996;17:445-452.

Yokoyama K, Nakagawa H, Wittkampf FHM, Pitha JV, Lazzara R, Jackman WM. Comparison of electrode cooling between internal and open irrigation in radiofrequency ablation lesion depth and incidence of thrombus and steam pop. Circulation. 2006;113:11-19.

European Examination Report issued in EP Application No. GB1202636.5, mailed May 26, 2015, 2 pages.

\* cited by examiner

SYSTEM AND METHOD FOR PREDICTING LESION SIZE SHORTLY AFTER ONSET OF RF ENERGY DELIVERY

This application claims the benefit of priority from U.S. Provisional Application Ser. No. 61/242,642, filed on Sep. 15, 2009, entitled "System and Method for Predicting Lesion Size Shortly After Onset of RF Energy Delivery," which is hereby incorporated by reference as if set forth in its entirety herein.

FIELD OF THE INVENTION

The present invention relates to cardiac ablation treatment, and, more particularly, to systems and methods for ablation lesion size prediction shortly after the onset of delivery of RF energy.

BACKGROUND OF THE INVENTION

Cardiac arrhythmias that originate from a focal area or depend upon a discrete circuit can be eliminated by catheter ablation. Various energy sources are utilized for this purpose of which radiofrequency (RF) energy at a frequency of 200 kHz-500 kHz is most commonly employed and is delivered to electrodes on the tip of a catheter. Heating occurs due to power dissipation within the tissue of the energy delivered by the electrodes. Power density decreases in relation to the square of the distance from the electrode.

The amount of RF energy delivered is usually controlled by preset temperature measured by a thermal sensor embedded in the tip of the distal electrode. In many procedures, temperature is set to less than 70° C. prior to ablation and monitored for temperature rise after RF energy delivery begins. At electrode temperatures of about 100° C., blood and tissue can coagulate. Coagulation causes an increase in impedance which can be sufficient to impair further delivery of RF energy to underlying tissue. Thus, many ablation systems regulate electrode temperature as to mitigate this problem.

However, regulation of RF energy based on electrode temperature feedback does not accurately indicate the electrode interface temperature since electrode temperature is dependent on various parameters, including, for example, any cooling of the electrode surface by flowing blood. These parameters cause uncertainty in predictions of lesion size and so temperature in and of itself is not a viable predictor of lesion size.

In a previous publication, the inventors found that several biophysical parameters evaluated individually and measured at 120 seconds after onset of RF energy correlate with lesion depth and volume. He D, Bosnos M, Mays M, Marcus F., Assessment of Myocardial Lesion Size During in vitro Radiofrequency Catheter Ablation," IEEE Transactions in Biomedical Engineering 2003; 50(6): 768-776 ("IEEE TBE"). Two parameters, capacitance and resistance, which can be calculated from RF impedance and phase angle, were observed to have a greater relation to lesion volume than impedance alone.

The clinical success of cardiac tissue ablation to treat arrhythmias depends on efficacy and safety of the application of RF energy. Predicting lesion size is important to the success of the application of RF energy for a variety of ablation procedures, but has been difficult to achieve. Many factors influence lesion size such as tissue-electrode contact force, ablation energy level, cooling factors (i.e., blood flow rate), tissue perfusion and the duration of energy delivery. In addition, there are other factors that can limit deep lesion formation, such as early impedance rise that can prevent continued energy delivery, as noted above.

Tissue ablation technology utilizes catheter tip temperature monitoring with feedback control to titrate energy delivery. The limitations of this approach are that the catheter tip temperature and tissue temperatures are not the same. The catheter tip temperature is consistently higher than tissue temperature. The difference is variable and is dependent on the force of the catheter tissue contact that determines impedance as well as cooling of the catheter tip. To predict lesion size, Stagegaard et al. proposed measuring the rise of impedance when the catheter tip is placed against the cardiac tissue before ablation combined with the rise of catheter tip temperature during 5 seconds of RF energy delivered at 0.6 watts. Stagegaard N, Petersen H H, Cehn X, Svendsen J H., Indication Of The Radiofrequency Induced Lesion Size By Pre-Ablation Measurements, Europace 2005; 7:525-534. However, this method is not applicable to irrigated catheters in which the catheter tip temperature is much lower than tissue temperature. When using such catheters, there is a risk of popping and perforation. An irrigated catheter ablation system applies energy in the power mode based on the empiric experience of the operator. There is no accurate catheter tip temperature control system for an irrigated ablation system known to the inventors.

Results obtained in connection with the inventors' previous study reported in IEEE TBE show that when the electrode-tissue contact area has cooled, 120 seconds after RF energy ceases, there is a relatively small return to baseline of the capacitance parameter (14.3%) compared to temperature sensitive impedance (76.4%). This observation supports this parameter indicating tissue change.

What remains needed in the art are systems that are adapted to predict lesion size shortly after the onset of RF ablation procedure commencing and provide such predictions to the operator to inform the procedure. What is further needed in the art are methods that provide accurate predictions of lesion size within seconds of the onset of the delivery of RF energy. Such a system and method are desirable for use with irrigated catheters. The present invention can be implemented to address any or all of these needs.

SUMMARY OF THE INVENTION

In accordance with a broad aspect of the invention, a system for predicting lesion size or volume so as to inform or control an ablation procedure is provided in which the prediction and/or control is made without regard to an actual detected temperature in the vicinity of the ablation electrodes. As a consequence, the present control system has utility in certain applications such as with irrigated ablation procedures which, because of the local irrigation in the vicinity of the ablation site, have created difficulties when using conventional control solutions.

In accordance with a more particular aspect of the invention, a computer-implemented control system is adapted to predict a lesion size in tissue shortly after the onset of an RF ablation procedure of the type that uses an ablation catheter to access tissue within a patient. A computer has a processor that executes a plurality of modules that configure the process to perform specified functions. A data acquisition system has multiple channels that provide data, including at least one channel providing data from at least one ablation electrode on the ablation catheter. A temperature determining module is configured to detect a temperature from at least one temperature sensor on the ablation catheter and includes a control loop operatively responsive to the detected temperature to control a rise time to a target temperature. An RF control module is operative to vary an RF generator output so as to maintain the target temperature for a duration of the RF ablation procedure. A regression algorithm is operative to apply a formula and compute the prediction of the lesion size in the tissue, shortly after the onset of the RF ablation procedure, independent of the detected temperature from the at least one temperature sensor. A user-interface module is operative to provide onto a display at least the prediction of the lesion size to inform the RF ablation procedure.

Advantageously, the system can implement such a control system to automatically control RF energy delivery so as to achieve a target lesion size in view of the tissue response after the first few seconds of energy delivery after the onset of the RF ablation procedure.

In one implementation, the data acquisition system is incorporated into an RF generator. A further degree of integration can have the data acquisition system, the RF generation, and the functionality of the various modules described herein managed by programming in the processor of the computer.

In a related aspect, such a control system can be configured to support ablation systems that utilize ablative energy sources other than RF, such as cryogenic energy or ultrasound energy sources.

These and other aspects, features, and advantages of the present invention, some of which are detailed in the claims attached hereto, can be further appreciated from the following discussion of certain embodiments of the invention taken together with the drawing figures that illustrate the embodiments thereof.

BRIEF DESCRIPTION OF THE DRAWING FIGURES

DETAILED DESCRIPTION OF CERTAIN EMBODIMENTS OF THE INVENTION

By way of overview and introduction, an experimental apparatus was constructed to test certain mathematical transformations of biophysical parameters obtained from an in vitro sample of cardiac tissue in support of a system and method configured for use in a real-time, in vivo electrophysiological procedure. The experimental apparatus provided data to a data collection system constructed in accordance with an embodiment of the invention in order to obtain certain electrical data relating to a tissue's response to the delivery of RF energy and to process that data so as to derive and output biophysical parameters based on that procedure.

The in vitro study that supported this work used a combination of several biophysical parameters to predict tissue lesion formation during the early phase of energy delivery. These parameters reflect tissue property changes in real-time regardless of thermal readings. This approach enhances the safety and efficacy of ablation procedures, since the extent of lesion formation can be predicted, when such parameters are used, as early as about 5 seconds after onset of RF energy. This prediction can be reported to the operator so he or she can decide whether to continue or pause energy delivery and/or adjust either the electrode position, the electrode-tissue contact force, or both. Likewise, the prediction provided by a system in accordance with the invention can provide a basis for automated control of RF energy delivery so as to achieve a target lesion size or volume in view of the tissue response to the first few seconds of energy delivery. Moreover, the mathematical transformations of the obtained biophysical parameters can be used to gauge lesion formation shortly after the onset of the ablation procedure independent of the ablation technique being performed. As a result, for example, the determinations of phase angle differences, as discussed hereinbelow, are relevant to lesion formation prediction for RF ablation procedures and for procedures conducted using other ablation techniques.

Figure 1:
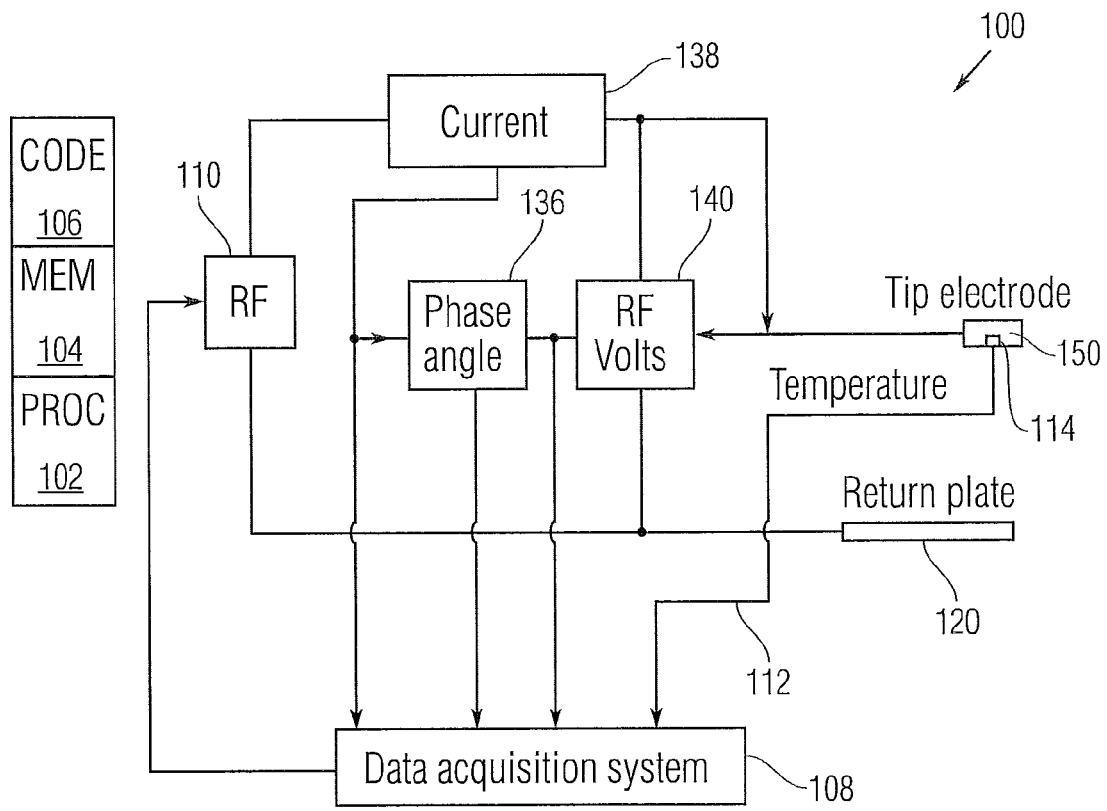
FIG. 1 is a schematic diagram of a data acquisition system in accordance with one embodiment of the invention.

Referring first to FIG. 1, a data collection system ("DCS") 100 includes a processor 102, memory 104, and code 106 executing in the processor to configure the processor for measurement and processing of biophysical parameters obtained from an indwelling catheter (not shown) having at least one temperature sensor 114, a tip electrode 150 for delivering RF energy to tissue, and a return electrode 120. The DCS 100 has at least portions of the code 106 executing therein to provide the functionality described below. Other portions of the code 106 can reside in the memory 104 until needed. The memory can take on a variety of forms known in the art such as RAM, ROM, and magnetic and optical storage devices.

The code 106 can be executed in the processor of a dedicated device, or another device used in an ablation system, such as a processor of an RF generator or other ablation energy source. For instance, the ablation energy source can include a processor that implements the functionality of the code 106 described herein, as well as other functionality related to providing an output of ablative energy.

The DCS 100 includes a 12-bit, 16-channel data acquisition system 108 (Data Translation). For instance, the data acquisition system ("DAS") can comprise a stand-alone system, or functionality included with the LabSystem Pro available from C. R. Bard, Inc., or functionality included in the RF generator. The DAS acquires data from multiple channels, such as from probes that can be attached to various indwelling electrodes (e.g., tip electrode 150) and external electrodes, as are conventionally employed in electrophysiology procedures. The number of bits and the number of channels provided by the DAS and used in a given embodiment can be varied to accommodate the requirements of a particular implementation.

Figure 1A:
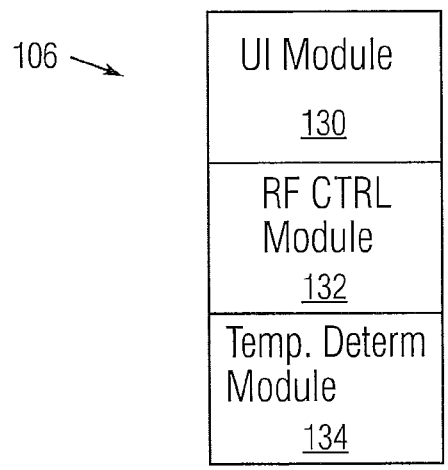
FIG. 1A is a schematic diagram of a set of code modules that configure a processor to operate upon data and derive one or more biophysical parameters, in accordance with one embodiment of the invention.

Referring now to FIG. 1A, the code 106 includes a user-interface module 130 that, when executed in the processor, configures the DCS to display, on an output device such as a computer monitor, the measured parameters from a previous study or from a real-time procedure. The parameters that can be displayed, include, without limitation, electrode temperature, unipolar RF voltage, power, phase angle, impedance (e.g., 300 kHz) and 5 kHz bipolar impedance (see FIG. 3 for a presentation on a display 300). Whether displaying historical data or real-time data, the data can be recorded every 100 ms of a procedure, for example, every 100 ms of a 120 second procedure in which there is pulsed RF delivery of energy to tissue. At a 50% duty cycle, such a procedure has 60 seconds of time in which RF energy is being delivered.

A portion of the code 106 includes an RF control module 132 that is operatively connected to a linear amplifier 110 that produces, say, a 300 kHz pulsed, sinusoidal RF output. The RF voltage output by the linear amplifier is varied under control of the RF control module so as to maintain a desired (set) target temperature. More generally, an ablation energy output can be generated and used by the system as a pulsed output, or as a continuous wave.

For example, in a continuous wave mode of operation, the duty cycle is 100%, and the length of the procedure can be shortened or lengthened, as compared to the example set forth above, yet the phase angle determinations and other parameters described herein remain predictive of the lesion size (or volume) formation. As will be understood by those of ordinary skill in the art of regression computations, the coefficients utilized by the regression algorithm described below are adjusted in a conventional manner to compensate for changes in procedure time, duty cycle, frequency of the ablation energy, bi-polar verses unipolar operation, and so on.

The target temperature is determined by a portion of the code 106 that comprises a temperature determining module 134 that implements a proportional, integral & differential (PID) control loop in which an electrode thermocouple signal 112 is the input. The thermocouple signal is typically provided from one or more thermocouples embedded in the tip electrode 150, but a similar signal can be provided by a temperature sensor of different design, and also by sensors that are adjacent to one or more electrodes, such as sensor/thermocouple 114 shown in FIG. 1. At least one temperature sensor can be associated with each electrode 150-158 supported on a given catheter construction. The PID includes coefficients that can be selected, for example, to hasten the rise time of the target electrode temperature and minimize overshoot of the target temperature. As such, the time to peak-power is determined, in part, by the PID coefficients that were selected and used by the temperature determining module 134.

The DCS 100 further includes a phase-angle circuit 136 that determines the phase angle between the current waveform and voltage waveform of energy delivered to a particular electrode, such as the catheter's tip electrode. The circuit determines overlap by measuring a proportion of time that the RF voltage waveform overlaps the RF current waveform. The overlap is determined with reference to the zero crossing of the current waveform relative to the zero crossing of the voltage waveform. In particular, the current is measured at location 138 in the series circuit comprising the RF source 110, the tip electrode 150, the return electrode 120 and back to the RF source 110. The voltage is measured via a parallel connection across the tip electrode 150 and the return plate 120. The circuit can be implemented as a portion of the code 106 that emulates the actions of such an analog circuit. In that alternative mode, the code module is first coupled to analog-to-digital signal converters (and other conventional circuitry) so that the current and voltage waveforms, their zero-crossing times, and their proportion of overlap can be processed digitally. Another alternative can be employed free of any analog to digital converters. In this alternative, a timer module is configured to measure the time between the respective zero crossings of the current and voltage waveforms. The timer module can be sampled, as needed, to collect the time difference between the respective zero crossings and this information used to compute phase differences in view of the frequency of the ablation energy being used.

The phase-angle circuit 136, in like manner, can determine the phase angle between the current waveform and voltage waveform delivered to an impedance-sensing electrode. This arrangement is useful with a catheter that is constructed to deliver ablative energy using a device other than the electrode. One such catheter construction has an ultrasound transducer to deliver ablative energy, and an impedance sensing electrode, constructed such as any of electrodes 150-158 (see FIG. 6), provided for the purpose of contacting tissue and permitting impedance measurements therewith. The impedance-sensing electrode can deliver current and voltage waveforms to permit a determination of phase differences in the manners described above.

The portions of code 106 can be programmed in a variety of languages for use on a selected operating system. As one non-limiting example, the code 106 can comprise software programmed in Microsoft Visual Basic for execution on a processor operating a Windows 95, XP, or 7.0 operating system.

In use, the DCS monitors ablation energy that is applied to tissue, such as in an in vivo procedure using an ablation catheter, obtains RF voltage, RF current, and temperature data from the indwelling electrode, and derives impedance, capacitive reactance, and resistance and then applies those values to a regression algorithm to arrive at a predicted lesion volume at one or more times shortly after the onset of RF energy delivery to target tissue.

Figure 2:
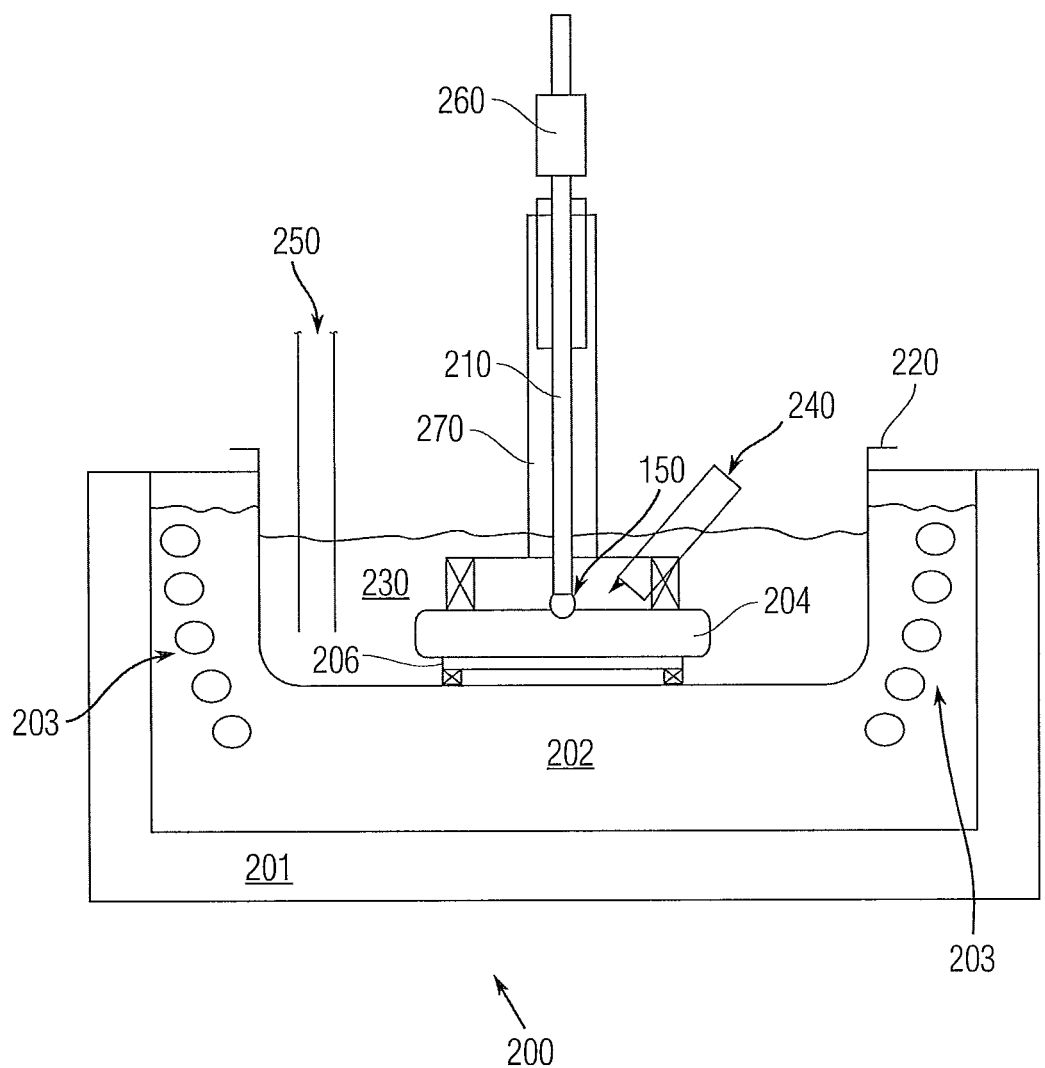
FIG. 2 illustrates an experimental apparatus showing a catheter holder and a catheter both in a perpendicular orientation so as to have a tip in contact with a cardiac tissue sample immersed in a pulsatile blood bath.

Referring now to FIG. 2, an experimental apparatus 200 is described that is useful for determining or confirming biophysical parameters of interest for prediction of lesion formation. Fresh bovine myocardium is preserved in an iced Krebs solution 202, e.g., a 37° C. water bath. A heat exchanger 203 is disposed in the water bath to regulate the Krebs solution, and the solution is supported within an insulated box 201. In the experimental apparatus, the tissue 204 comprises the left ventricle of the bovine myocardium and has been cut across its short axis in 1.5 cm slices. The tissue 204 is further cut into 3×10 cm rectangles and placed in a fixture 206 that holds a catheter 210 in contact with the tissue. The tissue 204 is immersed in a metal pan 220 containing fresh, heparinized bovine blood 230 maintained at 37° C. The pan 220 also functions as the return electrode 120, returning RF energy from the tip electrode 150 via the (conductive) fixture 206. Pulsatile blood flows across the electrode-tissue interface region at a rate of 0.7 L/min due to action of a pump 240. An aspirator 250 can be provided to suck the blood 230 and operate in conjunction with the pump 240 to emulate blood flow. The catheter is placed on the ventricular endocardium and oriented perpendicular to the tissue surface (for this experimental arrangement) under a weight 260 of approximately 15 grams. The catheter 210 is held by a stand 270 that maintains the orientation of the catheter relative to the tissue during the in vitro experiments.

In connection with the in vitro experiments described herein, ablation energy was applied to bovine heart tissue in ninety-one trials on tissue from 5 (bovine) hearts and subsequently analyzed. In particular, unipolar pulsed RF energy at a frequency of 300 kHz was delivered to tip electrode 150. RF energy was applied for 500 ms of a one second pulse cycle followed by a 500 ms off period (50% duty cycle). Data was collected by the DCS 100 including the magnitude (i.e., absolute value) of RF voltage 140 delivered to the tip electrode, the magnitude of the RF current 138 delivered to the tip electrode, and the angle between the sinusoidal current and voltage waveforms based on their respective inflection points (which, in the absence of a DC bias is the zero-value crossing point of each waveform). From these values, impedance, capacitive reactance—namely, the component of impedance and phase angle which varies with frequency, and the resistance—namely, the component of impedance that does not vary with frequency, were calculated as follows:

Impedance=|RF voltage|/|RF current|

Capacitive Reactance=Impedance·(1+tan φ)

Resistance=Impedance·(1+tan φ)/tan φ, in which "/" is the divide symbol, "·" is the multiply symbol, "φ" is the angle between the sinusoidal RF current and RF voltage waveforms. These parameters (Impedance, phase angle of the unipolar 300 kHz RF current, RF voltage magnitude, RF current magnitude, Capacitive Reactance, Resistance, and power) were recorded during the RF on-phase. Electrode temperature was recorded during the entire cycle time.

In a continuous wave mode of operation, the electrode temperature and impedance measurements used in the formulas described herein can comprise average values over a measurement time since there is no RF "off"-phase.

To obtain a range of lesion sizes, RF energy was delivered in the constant temperature mode with electrode temperatures in the range of 45 to 65° C. Target temperatures for this study were chosen to minimize the chances of rapid impedance rise due to coagulation at the electrode-tissue interface. The temperature determining module 134 of the code 106 maintained the average electrode temperature. Parametric values were sampled every 100 ms and the heating and cooling slopes were measured during each pulse cycle (adjacent RF on/off times). Data was collected for 120 seconds while delivering pulsed-RF energy. The parametric values evaluated in this study were obtained at 5, 10, and 15 seconds after the onset of RF energy delivery. Measurements for calculating the final parameter changes were made at the beginning and 2 seconds before the termination of RF delivery.

Figure 3:
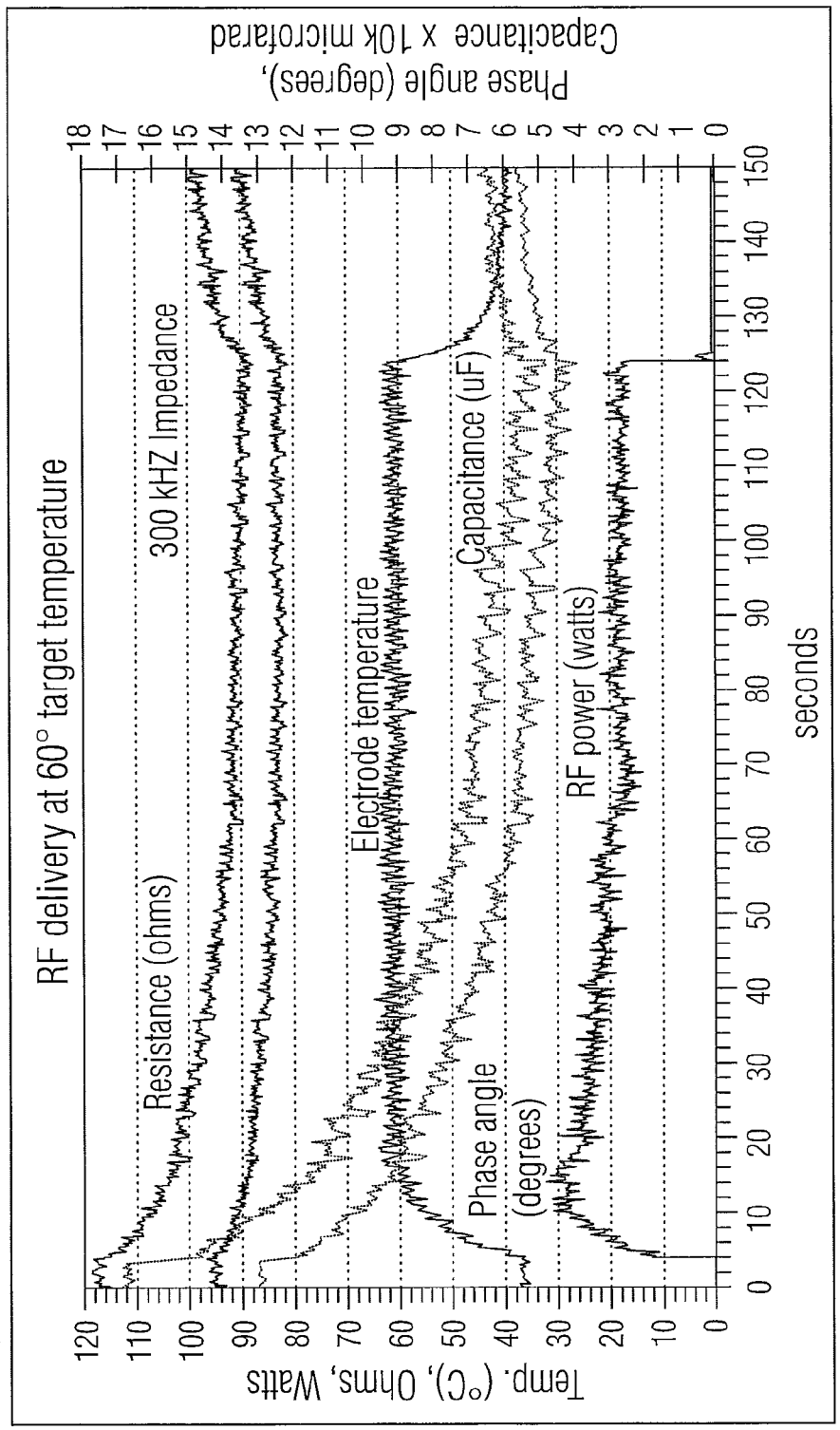
FIG. 3 is an example of obtained data and derived parameters during RF delivery of energy into cardiac tissue, including obtained data showing 300 kHz impedance and phase angle, applied RF power, and electrode temperature and derived parameters of capacitance and resistance.

FIG. 3 illustrates the results of collecting and calculating these parameters, which can be presented to the operator on a display associated with the system 100, if desired. The impedance, power, and phase angle can be calculated in real time and the resistance and capacitance parameters can be calculated immediately thereafter or off-line. FIG. 3 also illustrates the effect of pulsed RF energy on the electrode temperature can also be seen.

After in vitro ablation, the lesions were cut at the center of the unstained surface of the lesion to measure the maximum subsurface depth (D), length (L) and width (W). The tissue sample was then immersed in triphenyl tetrazolium chloride (TTC), at room temperature for 15 minutes, which causes the undamaged tissue surface to acquire a red/blue coloration that outlines the extent of the white/pink tissue damaged area. The TTC stain was prepared as 10% TTC by weight in Tris buffer at pH 7.5. Maximum subsurface lesion depth and width (W) were measured. RF lesions typically have an ellipsoid shaped depth (D) and these measurements were used to calculate lesion volume using the formula for an ellipsoid:

$$\text{volume}=\pi\times(4/3)\times(D/2)\times W/2)\times(L/2)$$

The data collected from these experiments were analyzed to determine the variables that best predict the volume of the lesion. In particular, the inventors examined the change of different covariates singly or in combination at 5, 10 and 15 seconds after the onset of RF energy delivery. The inventors performed a stepwise, multiple-linear regression analysis with a full model on the following variables: percent change of 300-kHz unipolar, 5 kHz bipolar and 800 kHz bipolar (tip and first ring) impedance, resistance, phase angle and capacitance, maximum power (at that time), integral of power, time to peak power, heating and cooling magnitude, and time and slope parameters relating to the variation of electrode temperature during the pulse cycle. The regression formula for predicting lesion volume for such parameters is:

Predicted Lesion Volume=$A\times$300 kHz impedance+$B\times$Resistance+$C\times$Capacitive reactance+$D\times TC$ cooling difference+$E\times$Power+$G$     (1)

Note that G is not multiplied by any value, and as such is essentially a fixed offset.

As will be understood, if a different frequency RF source or duty cycle is used, or if a different ablation energy source is used, the coefficient A would change accordingly. Likewise, if an irrigation fluid is used, it will be understood that the coefficient D is impacted. An offset G (whether positive or negative) can be used to finally fit a set of coefficients to a given set of operative parameters for a given procedure. More generally, the relationship identified above expresses a weighted relationship between selected biophysical parameters and respective coefficients, with the coefficients being adjustable to accommodate different ablation procedure times, bipolar operation, and so on. The use of cooling differences provides greater accuracy to lesion prediction, and can be used in certain implementations, and omitted from others. By providing the operative parameters to the Stata software, discussed next, suitable coefficients can be identified by a person of ordinary skill in the art.

All data were collected at the specific time of interest, namely, at 5 sec., 10 sec., and 15 sec., using the statistical package, Stata SE V9.2 for Windows, to conduct the analysis. The full model uses the parameters studied previously as reported in the aforementioned IEEE TBE article and further includes the parameters in Table 1 below. A significance level of greater than 0.05 was the criterion for removal of a parameter from the model. The inventors performed a regression analysis for observations taken at 5, 10, and 15 seconds after onset of RF energy delivery, any outliers were removed, and the prediction was observed at 5, 10 and 15 seconds. From this investigation, parameters relating to tissue change (resistance and capacitance) as well as power, were identified as important to prediction of lesion size in the first several seconds of RF delivery.

For the intervals selected, namely 5 seconds, 10 seconds, and 15 seconds, the predicted lesion volume equation can have coefficients (weightings) such as shown below, though it will be appreciated that these values are one set of values that are suitable for lesion volume prediction at about each of these respective time points, and that the values stated need not be invoked with the same degree of precision.

5 seconds:

=1848.98×300 kHz imped.+856.52×Resist.−140.23×Capacitance React.+6.69×$TC$ cooling diff.+17.21×Power (5 s)−208.96

10 seconds:

=4725.78×300 kHz imped.−5256.43×Resist.+460.50× Capacitance React.+44.59×*TC* cooling diff.+ 7.34×Power (10 s)−310.16

15 seconds:

=5017.75×300 kHz imped.−5295.15×Resist.+397.70× Capacitance React.+31.11×*TC* cooling diff.+ 5.52×Power (15 s)−291.29

The coefficients in the equations above are obtained using the Stata software mentioned above. For instance, the instruction and input for the Stata software for the measurements at the 10 second mark that were used in the foregoing experiments are:

stepwise, pr(0.05): regress pinkvol z1chg10s zlochg10s rchg10s phchg10s
zhichg10s capchg10s tc1cooldif10s tc1heatdif10s tc1coolslp10s
tc1heatslp10s tc1cooldly10s tc1heatdly10s pwr10sec intgpwr_0_10 where:
pinkvol—pink volume obtained at the 120 seconds mark
z1chg10s—percent change of 300-kHz unipolar impedance
zlochg10s—percent change of the 5 kHz bipolar impedance
rchg10s—percent of change of resistance
phchg10s—percent of change of 300-kHz unipolar phase angle
zhichg10s—percent of change of the 800 kHz bipolar impedance
capchg10s—percent of change of capacitance
tc1cooldif10s—change in electrode temperature during the cooling period
tc1heatdif10s—change in electrode temperature during the heating period
tc1coolslp10s—slope of the cooling difference
tc1heatslp10s—slope of the heating difference
tc1cooldly10s—delay to temperature bottom due to preceding cooling phase
tc1heatdly10s—delay to temperature peak due to preceding heating phase
pwr10sec—power at that time
intgpwr_0_10—Integral of power since onset of RF energy application As will be appreciated, coefficients for the equations above at different time intervals, such as at 5 sec., 15 sec. or at times around these values, can be obtained using the Stata software and suitable input settings that capture values not at 10s but at a different time (e.g., zhichg4.5s for a 4½ second interval). Table 1 shows the five best predictors of lesion size at 5, 10 and 15 seconds as determined after a stepwise analysis of the obtained data and derived parameters under investigation. The term "TC cooling difference," as used herein, refers to the average difference between the maximum and minimum electrode temperature of 3 pulse cycles centered at the specific time. The variable "R" refers to the correlation coefficient after regression analysis.

TABLE 1

| Predictor | 5 sec | 10 sec | 15 sec |
|---|---|---|---|
| Impedance (300 kHz unipolar) | | X | X |
| TC cooling difference | | X | X |
| Resistance | X | X | X |
| Capacitive Reactance | X | X | X |
| Power at interval (e.g., 5 sec) | X | X | X |
| R of lesion volume | 0.799 | 0.877 | 0.882 |
| R of lesion depth | 0.729 | 0.720 | 0.732 |

As shown in Table 1 above, when the same best combination of predictors that were identified at 10 and 15 seconds were used to assess those at the 5 second mark, there was an R for lesion volume of 0.798 compared with 0.799 (as shown in the table) when using all of the best predictors at 5 seconds. Therefore, for the sake of simplicity as well as practicality in programming an RF delivery device, the combination of the 5 best predictors of lesion size at 10 and 15 seconds could also be used to predict lesion size when measured at 5 seconds.

Figure 4:
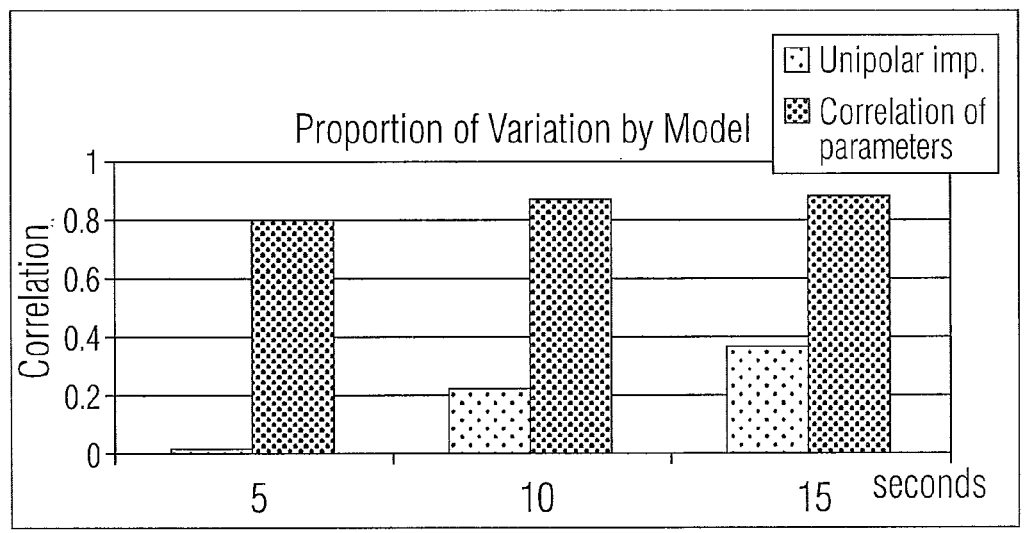
FIG. 4 is a graph to compare the correlation coefficient (R) at 5, 10 and 15 seconds of data obtained using only unipolar 300 kHz impedance data on the one hand and the combination of parameters applied to a regression algorithm, as proposed by the present inventors, on the other hand in regard to a prediction of lesion size.

The proportion of variation explained for lesion volume at 5, 10, and 15 seconds using only the 300 kHz unipolar impedance as a predictor were 0.016, 0.222 and 0.37 (see FIG. 4), respectively, while those for lesion depth at the same time points were 0.001, 0.1 and 0.188 respectively.

Figure 5:
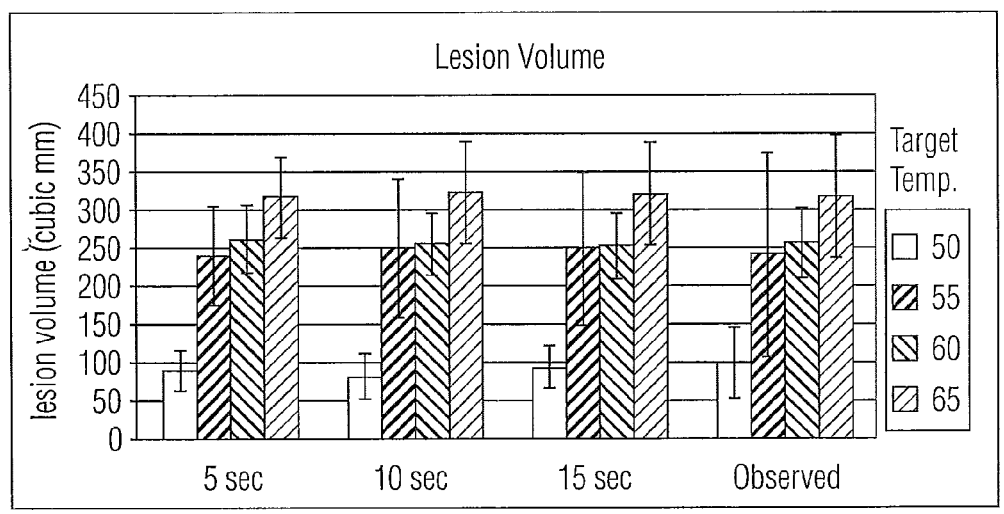
FIG. 5 is a graph to compare predicted (95% confidence interval) and observed lesion volume for a combination of parameters applied to a regression algorithm, as proposed by the present invention, at 5, 10 and 15 seconds by target temperature.

As shown in FIG. 5, the best prediction was observed at 15 seconds at which time the linear equation (1) explained about 76% of the variability of the lesion volume. The predicted values for lesion volume at different points in time were also compared with those observed at 120 seconds where the proportion of variation explained was 0.68. However, at the 5 second mark, the predicted value of the lesion volume was very close to the actual measured value, as can be seen in FIG. 5. More particularly, when using the combination of 300 kHz unipolar impedance, resistance, power at the interval in question (e.g., at the 5 second mark), and capacitance to predict lesion size, the explained variability was 71% at 5 seconds, and the prediction is reasonably close to the actual measured value at less than five seconds. The time to peak power can also be used as a parameter, which in other words is the rise time of the power signal relative to the coefficients of the PID algorithm.

The predicted lesion volume based on the algorithm (1) provides its prediction in regard to a combination of parameters that relate to biophysical changes in tissue properties, and so it should be applicable to other energy sources for tissue ablation, i.e. ultrasound and cryoablation. As well, the foregoing method for predicting lesion formation is applicable to irrigated catheter ablation as the regression formula is not dependent upon the detected temperature of the electrode, but only on the TC cooling difference.

It should appreciated that the TC cooling difference factor, while useful in the overall predicted volume computation, can be eliminated in certain implementations of the invention, such as when a more-minimal computational algorithm is desired for any reason.

In summary, there is no currently available technology to accurately predict ablation lesion size within seconds of onset of delivery of RF energy. However, after in vitro evaluation of changes in several biophysical characteristics of cardiac tissue within 5-15 seconds of the onset of RF energy, accurate predictions can be had as to lesion formation at 120 seconds, and even sooner with a regression algorithm adjusted for a shorter ablation procedure. RF energy was applied with a 50% duty cycle to measure heating and cooling behavior of the electrode temperature sensor. Changes in impedance, phase angle and the resulting resistance and capacitance, and power during RF ablation were analyzed. As a result, a combination of electrical based parameters measured early in the procedure, say, at about 5 seconds after onset of RF energy, was found in vitro to explain 71.7% of variability of lesion volume. Thus, a combination of these parameters provides better correlation with lesion formation than use of a single parameter and a system configured to process these parameters can be provided to predict lesion size during RF ablation in vivo shortly after the onset of RF energy delivery.

Figure 6:
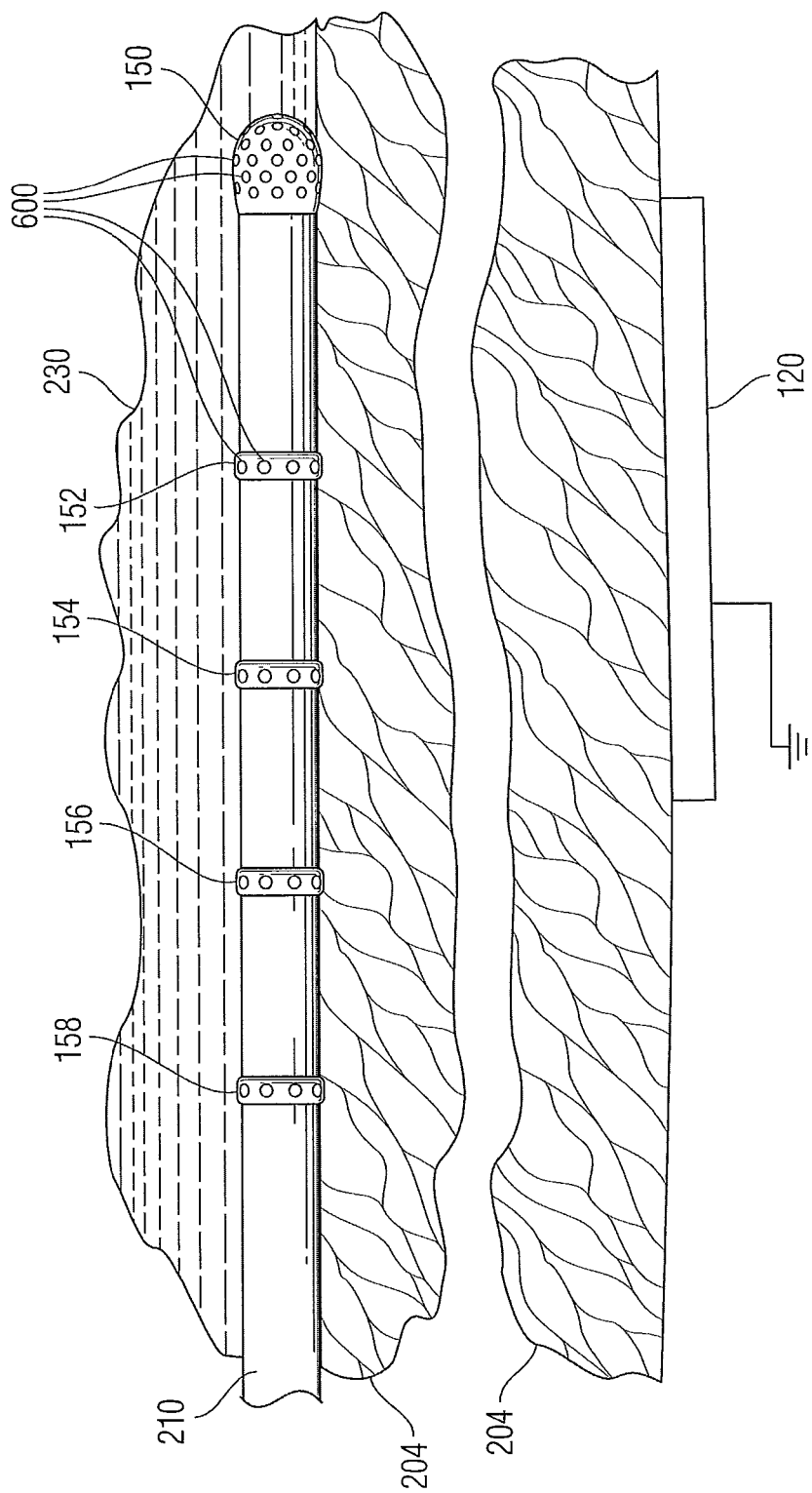
FIG. 6 illustrates an irrigated catheter disposed in vivo that can be used with the data acquisition system of the present invention.

Referring now to FIG. 6, an irrigated catheter is illustrated in position within a patient, with one side seated against tissue 204 (such as a result of steering, anchoring, or other controlled placement) and another side exposed to a blood pool 230. The catheter 210 includes a tip electrode 150 and a set of ring electrodes 152, 154, 156, and 158. Fewer or additional ring electrodes can be provided, and their respective, relative spacing varied. The electrodes can transmit ablation energy between one another or from each electrode toward a backplate 120, as is understood in the art.

It is known that for a given electrode side and tissue contact area, the size of a lesion created by radiofrequency (RF) energy is a function of the RF power level and the exposure time. At higher powers, however, the exposure time can be limited by an increase in impedance that occurs when the temperature at the electrode-tissue interface approaches 100° C. One way of maintaining the temperature less than or equal to this limit is to irrigate the ablation electrode with saline to provide convective cooling so as to control the electrode-tissue interface temperature and thereby prevent an increase in impedance. This can be done by introducing an irrigation fluid (typically, cooled saline) to the vicinity of all or the active ablation electrodes on the ablation catheter.

To introduce the fluid, a fluid lumen (not shown) is provided inside shaft portion of the catheter that transports the irrigation fluid from the proximal end of catheter 210 to distal end region (as shown in FIG. 6). The irrigation fluid can be dispersed into the vicinity surrounding distal end through apertures, such as apertures 600 provided in each of the electrodes 150-158. For further details on irrigation, see U.S. Published Application No. 2010-0152727 for "Irrigated Catheter," which is assigned to the present assignee. Alternative arrangements can be as shown in U.S. Pat. No. 7,727,229 (describing a braided conductive electrode arrangement with perfusion in the same region as the braided electrode), assigned to the present assignee, which is hereby incorporated by reference in its entirety. Alternatively, perfusion of an irrigation fluid can be achieved using a separate instrument than the ablation catheter itself. More generally, the irrigation holes 600 can have multiple holes ranging from, say, about six holes to about fifty-six holes on a tip electrode.

The presence of the irrigation fluid can have an adverse impact on conventional control systems that rely directly upon measured or detected temperature in the vicinity of the electrodes. However, the regression algorithm described herein is not dependent upon the detected temperature of the electrode, but rather is preferably configured to be responsive to the TC cooling difference, namely, an average difference between a maximum and a minimum electrode temperature that is detected over pulsed cycles centered about a particular prediction time. It is this difference computation rather than the temperature itself that is multiplied by a coefficient to provide a temperature-related component of the predicted lesion size (or volume), and this prediction is then available for use in controlling the ablation procedure so as to achieve a target lesion size (or volume) in the manner described above.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

We claim:

1. A computer-implemented control system adapted to predict a lesion size in tissue after the onset of an RF ablation procedure, the procedure being conducted using an RF generator output to drive at least one ablation electrode supported on the distal section of a catheter, the catheter further having at least one temperature sensor, comprising:
   a computer having a processor;
   a data acquisition system having multiple channels that provide data, including at least one channel providing data from the at least one ablation electrode;
   a plurality of modules each executing in the processor of the computer, including:
   a temperature determining module comprising a detection of temperatures in the vicinity of the at least one ablation electrode from the at least one temperature sensor and a control loop operatively responsive to a currently detected temperature of the temperatures to control a rise time to a target temperature;
   an RF control module operative to vary the RF generator output so as to maintain the target temperature for a duration of the RF ablation procedure;
   a regression algorithm operative to apply a formula and compute the prediction of the lesion size in the tissue, within five seconds after the onset of the RF ablation procedure, independent of the currently detected temperature from the at least one temperature sensor; and
   a user-interface module operative to provide from the computer onto a display at least the prediction of the lesion size to inform the RF ablation procedure.

2. The control system of claim 1, wherein the formula used by the regression algorithm comprises a weighted combination of impedance, resistance, capacitive reactance, power and an average difference between a maximum and a minimum electrode temperature detection over pulsed cycles centered about a particular prediction time.

3. The control system of claim 2, wherein the weighted combination in the formula used by the regression algorithm further comprises an offset.

4. The control system of claim 3, wherein the weighted combination in the formula used by the regression algorithm further comprises a weighting of a time to peak power.

5. The control system of claim 3, wherein the formula comprises solely the weighted combination of impedance, resistance, capacitive reactance, power, the offset, and the average difference between the maximum and the minimum electrode temperature over pulsed cycles centered about the particular prediction time.

6. The control system of claim 1, wherein the control loop of the temperature determining module comprises a proportional, integral and differential (PID) control loop.

7. The control system of claim 6, wherein the PID control loop has coefficients selected to hasten a time to peak-power delivery while concurrently minimizing overshoot of the target temperature.

8. The control system of claim 1, wherein the RF generator output is in a range of 300 to 500 KHz.

9. The control system of claim 1, further comprising a phase angle circuit or module, wherein the phase angle circuit or module computes a phase angle between an RF voltage and an RF current from which a capacitive reactance and a resistance can be derived.

10. The control system of claim 1, wherein the RF control module is responsive to the regression algorithm to automatically control RF energy delivery so as to achieve a target lesion size in view of the tissue response.

11. A computer-implemented control system adapted to predict a lesion size in tissue after the onset of an RF ablation procedure that is conducted using an RF generator output, comprising:
- an irrigated catheter having a distal section that supports at least one ablation electrode and at least one temperature sensor, and a fluid lumen extending the length of the irrigated catheter sized to deliver an irrigation fluid in the vicinity of the at least one ablation electrode;
- a computer having a processor;
- a data acquisition system having multiple channels that provide data, including data from the at least one ablation electrode;
- a plurality of modules each executing in the processor of the computer, including:
- a temperature determining module comprising a detection of temperatures in the vicinity of the at least one ablation electrode from the at least one temperature sensor and a control loop operatively responsive to a currently detected temperature of the temperatures to control a rise time to a target temperature;
- an RF control module operative to vary the RF generator output so as to maintain the target temperature for a duration of the RF ablation procedure;
- a regression algorithm operative to apply a formula and compute the prediction of the lesion size in the tissue, within five seconds after the onset of the RF ablation procedure, independent of the currently detected temperature from the at least one temperature sensor; and
- a user-interface module operative to provide from the computer onto a display at least the prediction of the lesion size to inform the RF ablation procedure.

12. The control system of claim 11, wherein the formula used by the regression algorithm comprises a weighted combination of impedance, resistance, capacitive reactance, power and an average difference between a maximum and a minimum electrode temperature detection over pulsed cycles centered about a particular prediction time.

13. The control system of claim 12, wherein the weighted combination in the formula used by the regression algorithm further comprises an offset.

14. The control system of claim 13, wherein the weighted combination in the formula used by the regression algorithm further comprises a weighting of a time to peak power.

15. The control system of claim 13, wherein the formula comprises solely the weighted combination of impedance, resistance, capacitive reactance, power, the offset, and the average difference between the maximum and the minimum electrode temperature over pulsed cycles centered about the particular prediction time.

16. The control system of claim 11, wherein the control loop of the temperature determining module comprises a proportional, integral and differential (PID) control loop.

17. The control system of claim 16, wherein the PID control loop has coefficients selected to hasten a time to peak-power delivery while concurrently minimizing overshoot of the target temperature.

18. The control system of claim 11, wherein the RF generator output is in a range of 300 KHz to 500 KHz.

19. The control system of claim 11, further comprising a phase angle circuit or module, wherein the phase angle circuit or module computes a phase angle between an RF voltage and an RF current from which a capacitive reactance and a resistance can be derived.

20. The control system of claim 11, wherein the RF control module is responsive to the regression algorithm to automatically control RF energy delivery so as to achieve a target lesion size in view of the tissue response.

* * * * *